US00PP22247P2

(12) United States Plant Patent
Ferguson

(10) Patent No.: US PP22,247 P2
(45) Date of Patent: Nov. 15, 2011

(54) STRAWBERRY PLANT NAMED 'DRISSTRAWSIXTEEN'

(50) Latin Name: *Fragaria×ananassa*
Varietal Denomination: DrisStrawSixteen

(75) Inventor: Michael D. Ferguson, Moorpark, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 12/802,695

(22) Filed: Jun. 11, 2010

(51) Int. Cl.
*A01H 5/00* (2006.01)

(52) U.S. Cl. ..... Plt./208

(58) Field of Classification Search ..... Plt./208
See application file for complete search history.

*Primary Examiner* — Susan McCormick Ewoldt

(74) *Attorney, Agent, or Firm* — Jondle & Associates, P.C.

(57) ABSTRACT

This invention relates to a new and distinct variety of strawberry plant named 'DrisStrawSixteen'. The new variety is primarily characterized by a globose plant habit, strong vigor, and large-sized berries, is disclosed.

3 Drawing Sheets

Genus and species: *Fragaria×ananassa.*
Variety denomination: 'DrisStrawSixteen'.

BACKGROUND OF THE NEW PLANT

The present invention relates to a new and distinct strawberry variety designated 'DrisStrawSixteen' and botanically known as *Fragaria×ananassa*. This new strawberry variety was discovered in Ventura County, Calif. in January 2004 and originated from a cross between the proprietary female parent 'El Dorado' (U.S. Plant Pat. No. 16,238) and the proprietary male parent '12J277' (unpatented). The original seedling of the new variety was first asexually propagated at a nursery in Shasta County, Calif. in January 2004.

'DrisStrawSixteen' was subsequently asexually propagated at a nursery in Shasta County, Calif. and underwent further testing in Spain for two years. The present invention has been found to retain its distinctive characteristics through successive asexual propagations via stolons and tissue culture.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from four-month-old plants.

DESCRIPTION OF THE NEW VARIETY

Figure 1:
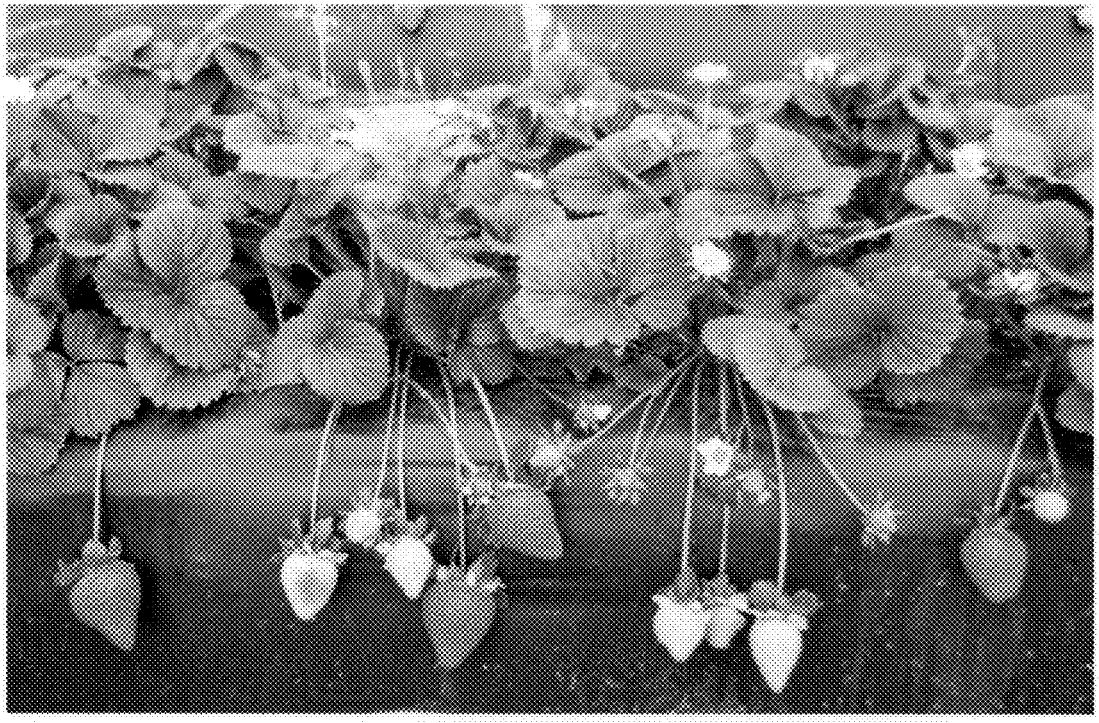
FIG. 1 shows overall plant habit including fruit at various stages of development.
Figure 2:
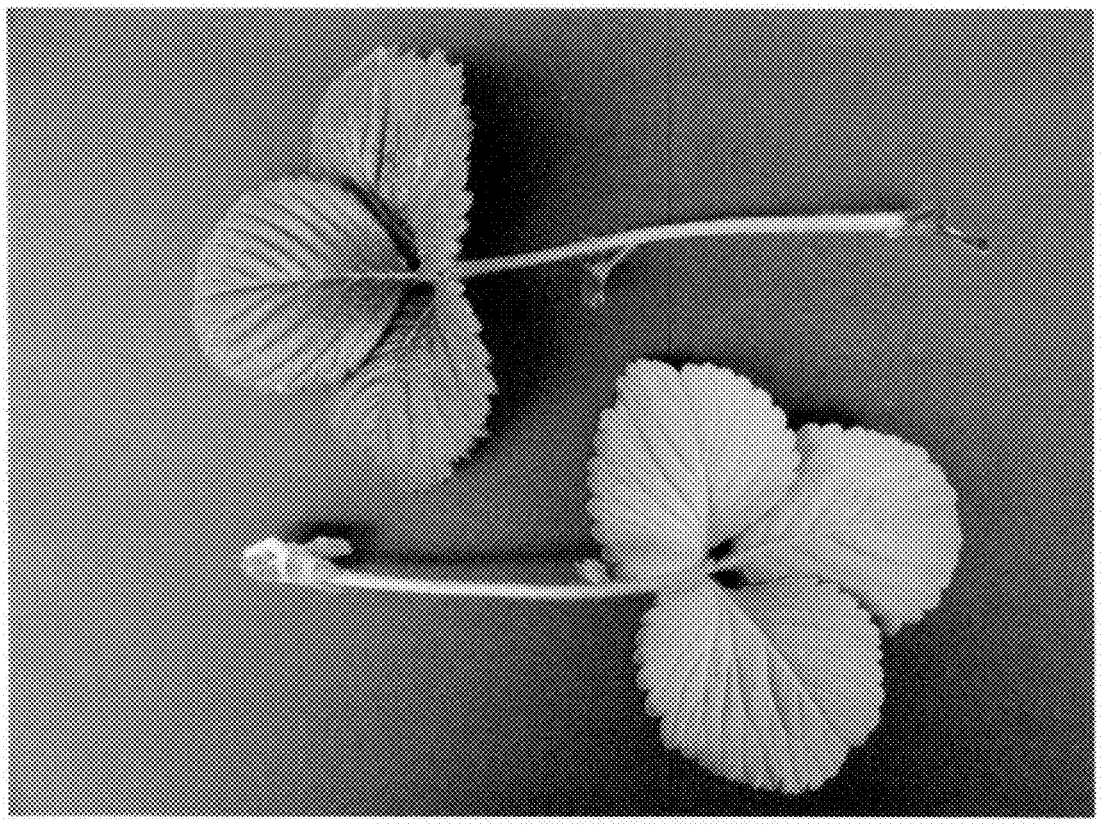
FIG. 2 shows leaves of the plant with three leaflets.
Figure 3:
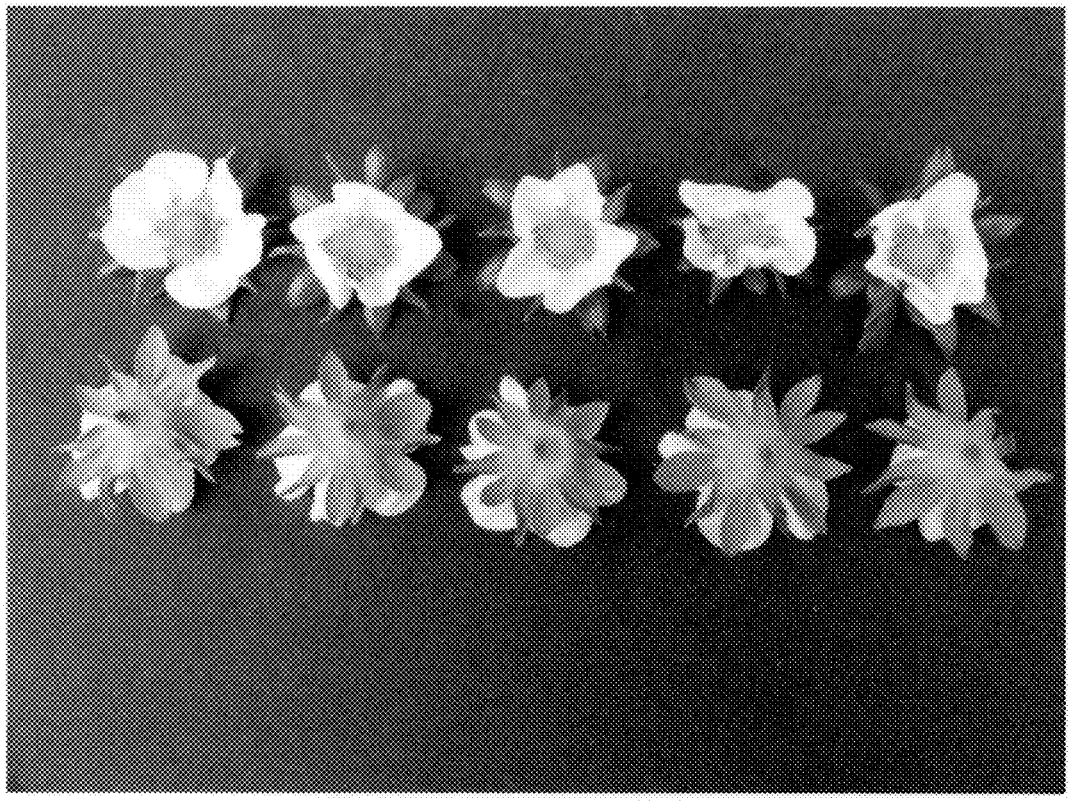
FIG. 3 shows both the upper surface and lower surface of several of the flowers.
Figure 4:
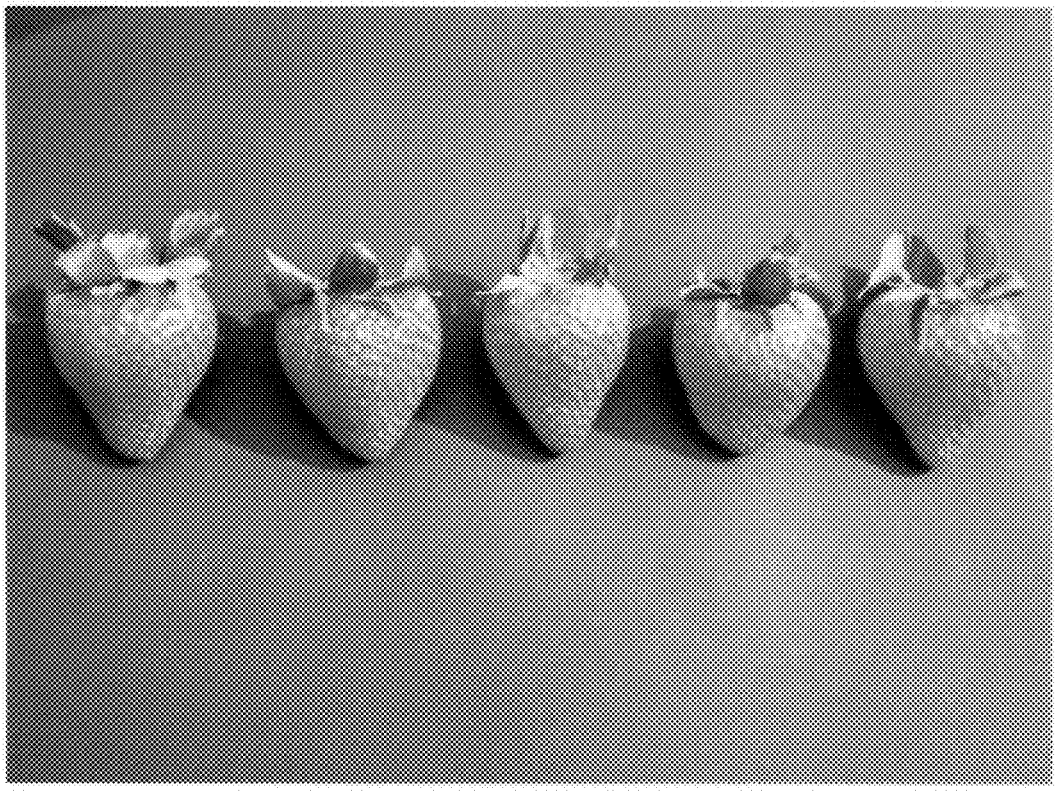
FIG. 4 shows the whole fruit.
Figure 5:
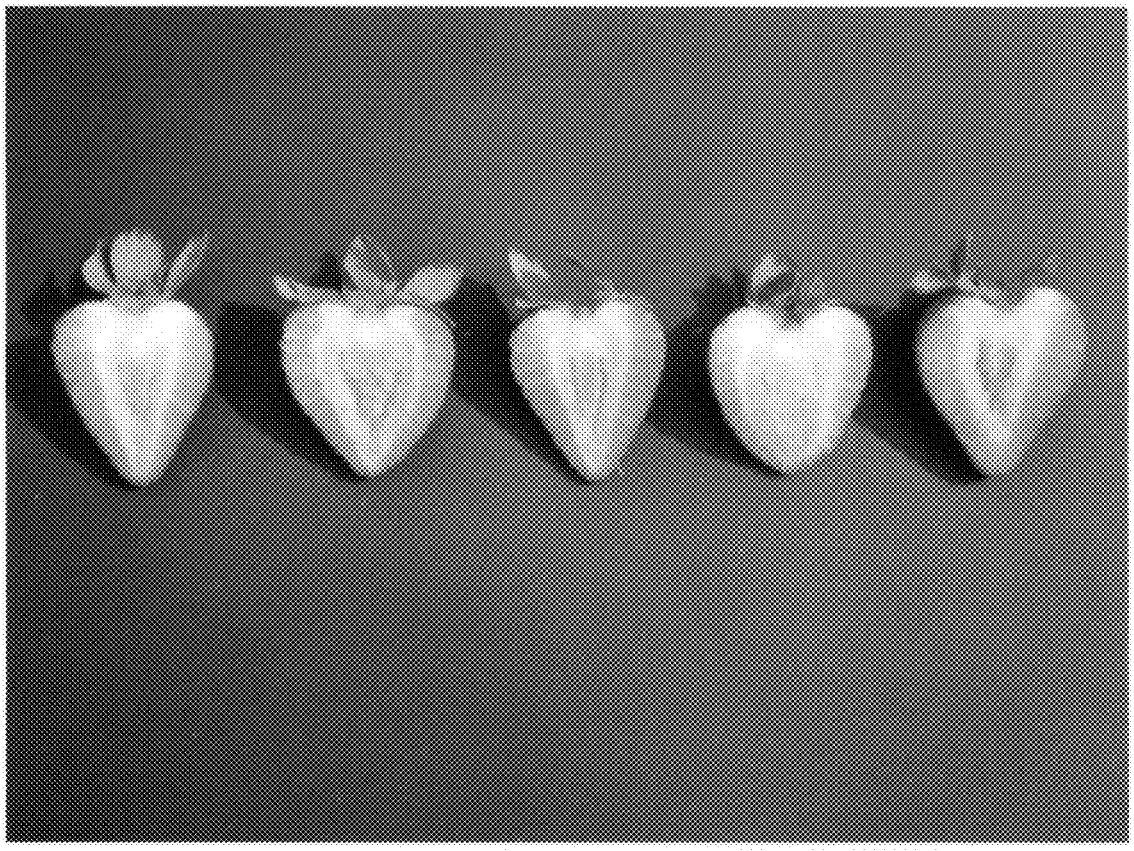
FIG. 5 shows the fruit in longitudinal cross-section.

The following detailed descriptions set forth the distinctive characteristics of 'DrisStrawSixteen'. The data which define these characteristics is based on observations taken in Spain from 2008 to 2009. This description is in accordance with UPOV terminology. Color designations, color descriptions, and other phenotypical descriptions may deviate from the stated values and descriptions depending upon variation in environmental, seasonal, climatic, and cultural conditions. 'DrisStrawSixteen' has not been observed under all possible environmental conditions. The botanical description of 'DrisStrawSixteen' was taken from four-month-old plants. Color terminology follows The Royal Horticultural Society Colour Chart, London (R.H.S.) (2001).

DETAILED BOTANICAL DESCRIPTION OF THE PLANT

Classification:
- *Species.*—*Fragaria×ananassa.*
- *Common name.*—Strawberry.
- *Denomination.*—'DrisStrawSixteen'.

Parentage:
- *Female parent.*—The proprietary female parent 'El Dorado' (U.S. Plant Pat. No. 16,238).
- *Male parent.*—The proprietary male parent '12J277' (unpatented).

Plant:
- *Height.*—19.9 cm.
- *Diameter.*—27.6 cm.
- *Number of crowns/plant.*—3.
- *Habit.*—Globose.
- *Density of individual plant.*—Medium.
- *Vigor.*—Strong.

Leaves:
- *Terminal leaflet length.*—6.63 cm.
- *Terminal leaflet width.*—5.99 cm.
- *Terminal leaflet length/width ratio.*—1.1.
- *Number of teeth/terminal leaflet.*—21.
- *Shape of teeth.*—Rounded.
- *Color.*—Upper surface: RHS N137A (Medium green). Lower surface: RHS 138A (Medium green).
- *Leaf shape in cross section.*—Convex.
- *Leaf blistering.*—Strong.
- *Leaf glossiness.*—Medium.
- *Number of leaflets.*—3 only.

*Terminal leaflet margin profile.*—Revolute.
*Terminal leaflet length/width ratio.*—As long as broad.
*Terminal leaflet shape.*—Orbicular.
*Terminal leaflet base shape.*—Obtuse.
*Terminal leaflet apex shape.*—Rounded.
*Petiole.*—Length: 15.2 cm. Diameter: 0.422 cm. Pubescence: Dense. Pose of hairs: Upwards. Color: RHS 144C (Medium yellow-green).

Petiolule:
*Color.*—RHS 144D (Light yellow-green).
*Length.*—0.670 cm.
*Diameter.*—0.210 cm.

Stipule:
*Length.*—3.1 cm.
*Width.*—1.629 cm.
*Pubescence.*—Sparse.
*Stipule anthocyanin coloration.*—Medium.

Stolon:
*Number.*—Few.
*Average number of daughter plants per plant.*—25 to 30.
*Stolon anthocyanin.*—Absent or very weak.
*Thickness.*—Thick.
*Pubescence.*—Sparse.

Inflorescence:
*Position relative to foliage.*—Above.
*Time of flowering* (*50% of plants at first flower*).—Medium.
*Flower size.*—Large.
*Diameter.*—2.77 cm.
*Petals.*—Shape: Orbicular. Apex: Rounded. Base: Rounded. Margin: Entire. Spacing: Overlapping. Length: 1.302 cm. Width: 1.298 cm. Length/width ratio: 1.0; as long as broad. Typical and observed petal number per flower: 6. Color (both surfaces): RHS 155C (White).
*Calyx.*—Diameter: 4.314 cm. Diameter relative to corolla: Larger. Inner calyx diameter relative to outer: Same size.
*Sepal.*—Shape: Elliptical. Apex: Convex. Margin: Entire. Length: 1.586 cm. Width: 0.931 cm. Typical and observed sepal number per flower: 12.
*Receptacle color.*—RHS N144C (Medium yellow-green).
*Anther color.*—RHS 153C (Medium yellow-green).

Fruiting truss:
*Length.*—27.7 cm.
*Diameter at base of truss.*—0.929 cm.
*Number of berries per fruiting truss.*—3.
*Attitude at first picking.*—Erect.
*Color at base of truss.*—RHS 144A (Medium yellow-green).

Fruit:
*Length.*—5.302 cm.
*Width.*—3.977 cm.
*Length/width ratio.*—1.3.
*Fruit hollow length.*—2.113 cm.
*Fruit hollow width.*—0.676 cm.
*Fruit hollow length/width ration.*—3.1.
*Fruit hollow center* (*size*).—Medium.
*Weight* (*per individual berry*).—39.0 g.
*Fruit ratio of length/maximum width.*—Longer than broad.
*Relative fruit size.*—Large.
*Predominant fruit shape.*—Conical.
*Difference in shape between primary and secondary fruits.*—Marked.
*Unevenness of fruit surface.*—Absent or weak.
*Fruit skin color.*—RHS 45A (Medium red).
*Evenness of fruit color.*—Even.
*Fruit glossiness.*—Medium.
*Insertion of achenes.*—Level with surface.
*Achene coloration* (*sunward side of berry*).—RHS N138B (Medium green).
*Achene coloration* (*shaded side of berry*).—RHS 139C (Medium green).
*Achenes per berry.*—372.8.
*Band without achenes.*—Narrow.
*Insertion of calyx.*—Level.
*Pose of calyx segments.*—Spreading.
*Size of calyx in relation to fruit.*—Larger.
*Adherence of calyx.*—Strong.
*Firmness of flesh.*—Medium.
*Color of flesh.*—RHS 45C (Medium red).
*Evenness of flesh color.*—Even.
*Distribution of flesh color.*—Marginal and central.
*Sweetness.*—Medium.
*Acidity.*—Medium.
*Texture when tasted.*—Fine.
*Type of bearing.*—Not everbearing.
*Grams of fruit/plant.*—900 g.
*Harvest interval.*—Late December to early June.
*Harvest maturity.*—Mid-season.

Disease and insect resistance:
*Botrytis fruit rot.*—Moderately susceptible.
*Powdery mildew.*—Moderately susceptible.

COMPARISON WITH PARENTAL AND COMMERCIAL VARIETIES

When 'DrisStrawSixteen' is compared to the proprietary female parent 'El Dorado' (U.S. Plant Pat. No. 16,238), 'DrisStrawSixteen' is not everbearing while 'El Dorado' is partially everbearing. In addition, 'DrisStrawSixteen' has a larger fruit size (length: 5.302 cm; weight: 39.0 g) than 'El Dorado' (length: 4.5 cm; weight: 22.8 g). Further, 'DrisStrawSixteen' has a marked difference in shapes between primary and secondary fruits, while 'El Dorado' has a slight difference. Finally, 'DrisStrawSixteen' is moderately susceptible to *Botrytis* fruit rot and Powdery mildew, while 'El Dorado' is susceptible to *Botrytis* fruit rot and moderately resistant to Powdery mildew.

When 'DrisStrawSixteen' is compared to the proprietary male parent '12J277' (unpatented), 'DrisStrawSixteen' has firmer fruit and a higher chill vigor than '12J277'.

When 'DrisStrawSixteen' is compared to the commercial variety 'Sabrosa' (U.S. Plant Pat. No. 16,558), the petiole pose of hairs for 'DrisStrawSixteen' is upwards, while the petiole pose of hairs for 'Sabrosa' is outwards. In addition, 'DrisStrawSixteen' has a marked difference in shapes between primary and secondary fruits, while 'Sabrosa' has a slight difference. Finally, 'DrisStrawSixteen' has fruit with medium sweetness, fine texture when tasted, and medium acidity, while 'Sabrosa' has fruit with a strong sweetness, coarse texture when tasted, and weak acidity.

I claim:

1. A new and distinct variety of strawberry plant as described and shown herein.

* * * * *